United States Patent [19]
Phillips et al.

[11] Patent Number: 5,268,229
[45] Date of Patent: Dec. 7, 1993

[54] SPINNERET ORIFICES AND FILAMENT CROSS-SECTIONS WITH STABILIZING LEGS THEREFROM

[75] Inventors: Bobby M. Phillips, Jonesborough; Jack L. Nelson, Johnson City; William A. Haile, Kingsport, all of Tenn.; Hugh A. Thompson, Fairfield, Ohio

[73] Assignee: Eastman Kodak Company, Rochester, N.Y.

[21] Appl. No.: 918,174

[22] Filed: Jul. 23, 1992

[51] Int. Cl.$^5$ ............................................. D02G 3/00
[52] U.S. Cl. .................................... 428/400; 428/397; 428/378; 425/72.2; 264/177.13
[58] Field of Search ............... 428/369, 397, 400, 378; 425/72.2, DIG. 217; 264/177.13

[56] References Cited
U.S. PATENT DOCUMENTS

| | | | |
|---|---|---|---|
| 3,551,275 | 12/1970 | Teng | 161/170 |
| 4,364,996 | 12/1982 | Sugiyama | 428/369 |
| 4,392,808 | 7/1983 | Phillips | 425/464 |
| 4,443,492 | 4/1984 | Roller | 427/44 |
| 4,707,409 | 11/1987 | Phillips | 428/397 |
| 4,712,366 | 12/1987 | Tsujimoto et al. | 57/245 |

FOREIGN PATENT DOCUMENTS 0223908  6/2987  European Pat. Off. .

Primary Examiner—George F. Lesmes
Assistant Examiner—Chris Raimund
Attorney, Agent, or Firm—John D. Thallemer; William P. Heath, Jr.

[57] ABSTRACT

This invention relates to spinnerets having orifices of unique cross-sections, the spinnerets being useful for extruding therethrough filaments having "U" and "E" shaped cross-sections with stabilizing legs. The use of strategically placed stabilizing legs allow the filaments to maintain the desired shape. The "U" shaped filament cross-section provides improved drainage over previous filament cross-sections.

21 Claims, 16 Drawing Sheets

SPINNERET ORIFICES AND FILAMENT CROSS-SECTIONS WITH STABILIZING LEGS THEREFROM

FIELD OF THE INVENTION

This invention relates to spinnerets having orifices of unique cross-sections, the spinnerets being useful for extruding therethrough filaments having "U" and "E" shaped cross-sections with stabilizing legs. The use of strategically placed stabilizing legs allow the filaments to maintain the desired shape. The "U" shaped filament cross-section provides improved drainage over previous filament cross-sections.

BACKGROUND OF THE INVENTION

Presently available absorbent articles such as diapers, sanitary napkins, incontinence briefs, and the like are generally very good at absorbing aqueous fluids such as urine and blood. However, during typical use such articles become saturated at the impingement zone while other zones removed from the impingement zone will remain dry. As a result, a substantial portion of the total absorbent capabilities of such articles remains unused. Thus, it is desirable to have a means for transporting the aqueous fluids from the impingement zone to other areas of the absorbent article to more fully utilize the article's total absorbent capability.

Filaments capable of spontaneously transporting aqueous fluids such as water offer improved drainage over other types of filaments such as those disclosed in European Patent Application 0223908 and in U.S. Pat. No. 4,443,492. European Patent Application 0223908 discloses thermally bonded webs composed of polyester, polypropylene, or polyethylene hydrophobic fibers which are coated with acrylic acid partially neutralized by alkali metallic salts and crosslinked simultaneously with polymerization to form webs coated in situ with superabsorbant polymer. The webs have increased absorption of fluid when used in a sanitary product such as a diaper, but the individual fibers of the web do not possess the ability to transport fluid from the crotch area to lesser utilized areas of the absorbent core.

U.S. Pat No. 4,443,492 describes the coating of cellulose fiber based material with a water soluble monomer which is converted into a water-absorptive polymer. This type of material has poor absorption performance because the monomer is able to penetrate inside the fiber base material and fill the capillaries between filaments. The mode of wicking in this prior art is totally in the capillaries between the fibers. The diameter of the capillaries is reduced by the coating. As the coating swells in the wet state the capillaries are blocked off.

The present inventors have discovered that certain filaments having "U" and "E" shaped cross-sections with stabilizing legs more efficiently transport and drain aqueous fluids than filaments capable of spontaneously transporting fluids having other shapes. For example, various H-shaped filament cross-sections have been disclosed. U.S. Pat. No. 4,707,409 describes H-shaped filaments extruded through an orifice defined by two intersecting slots and each intersecting slot in turn defined by three quadrilateral sections connected in series. Copending commonly assigned U.S. patent application Ser. No. 07/736,267, filed Jul. 23, 1991, also discloses H-shaped filaments. The problem with such H-shaped filaments, however, is that the parallel wall channels with flat bottoms and small corner sections hold onto fluids and thus inhibit drainage.

U.S. Pat. No. 4,364,996 discloses U-shaped filament cross-sections with projections. The projections, however, do not stabilize the curved sections of the fiber. Moreover, the U-shaped fibers described in U.S. Pat. No. 4,364,996 do not have straight sections In contrast, the present inventors have overcome such deficiencies with "U" and "E" shaped fibers with stabilizing legs. Such "U" shaped fibers have straight and curved sections but do not have small corner sections to hold on to fluids. Thus, the "U" shaped fibers of the present invention provide complete drainage. Such "E" shaped fibers provide a wider top area which allows for improved acquisition of fluids and additional channels which lead to increased vertical movement against gravity when compared to H-shaped fibers. The use of strategically placed stabilizing legs allow the fibers to maintain their shape.

SUMMARY OF THE INVENTION

Accordingly, it is one object of the present invention to provide "U" and "E" shaped filament cross sections with stabilizing legs which are capable of spontaneously transporting aqueous fluids.

Another object of the invention is to produce "U" and "E" shaped filament cross-sections with stabilizing legs which exhibit improved drainage.

A further object of the present invention is to provide spinnerets having "U" and "E" shaped orifices with stabilizing legs.

The present invention is directed to synthetic filaments having "U" and "E" shaped filament cross-sections with stabilizing legs which are capable of spontaneously transporting water on the surface thereof. The filaments satisfy the following equation $$(1 - X \cos \theta_a) < 0,$$

wherein
$\theta_a$ is the advancing contact angle of water measured on a flat film made from the same material as the filament and having the same surface treatment, if any, X is a shape factor of the filament cross-section that satisfies the following equation $$X = \frac{P_w}{4r + (\pi - 2)D}$$

wherein
$P_w$ is the wetted perimeter of the filament,
r is the radius of the circumscribed circle circumscribing the filament cross-section, and
D is the minor axis dimension across the filament cross-section;

said "U" shaped filament with stabilizing legs comprising a curved section containing stabilizing legs and two straight sections, wherein w', the width of the filament, is 3 to 15 microns; $\beta'$, the angle between the stabilizing legs, is 10° to 60°; $\mu$, the acute angle formed by intersection of extension of straight portions of the filament, is 0° to 70°; a', the length of the straight section of the filament is 50 to 200 microns; r, the linear distance between the ends of the straight sections of the filament, is 30 to 300 microns; s, the perpendicular distance from a line connecting the outer extremities of the straight sections and the concave surface of the filament, is 20 to 100 microns; t, the length of a stabilizing leg, is independently 3 to 15 microns; and n, the number of stabilizing legs, is 3 to 6; provided that when n is equal to 3 or 5, there is a stabilizing leg on the vertical axis of symmetry and the other stabilizing legs are substantially symmetrically spaced around the vertical axis of symmetry; and when n is equal to 4 or 6, the stabilizing legs are substantially symmetrically spaced around the vertical axis of symmetry; and said "E" shaped filament with stabilizing legs comprising a backbone, two outer ribs, an inner rib, two rib extensions and stabilizing legs, wherein w', the width of the filament, is 3 to 15 microns; $\lambda'$, the angle between a linear extension of an outer rib and rib extension, is 0° to 45°; $\alpha$, the angle between the backbone and an outer rib, is 90° to 120°; e', the length of a stabilizing leg as measured from a center point in the filament, is independently 1 to 15 microns; f', the length of the backbone of the filament including stabilizing legs located on each end, is 30 to 100 microns; i', the linear distance between the center of an outer rib and the center of the middle rib, is 8 to 50 microns; j', the linear distance between the point where the outer rib intersects the rib extension and the center of the backbone, is 15 to 100 microns; k', the linear distance between the extremity of the middle rib and the center of the backbone, is 15 to 150 microns; l', the linear distance between the point where the outer rib intersects the rib extension and the extremity of the stabilizing leg located on the backbone, is 18 to 115 microns; m', the linear distance between the extremity of rib extension and the point where the outer rib intersects the rib extension, is 15 to 100 microns; and n', the number of stabilizing legs, is 4 or 6; provided that when $\lambda'$ equals 0, n is 4.

The present invention is also directed to spinnerets having "U" and "E" shaped orifices with stabilizing legs.

BRIEF DESCRIPTION OF THE DRAWINGS

The invention will be more fully understood and further advantages will become apparent when reference is made to the following detailed description of the invention and the accompanying drawings in which.

DETAILED DESCRIPTION OF THE INVENTION

Figure 1:
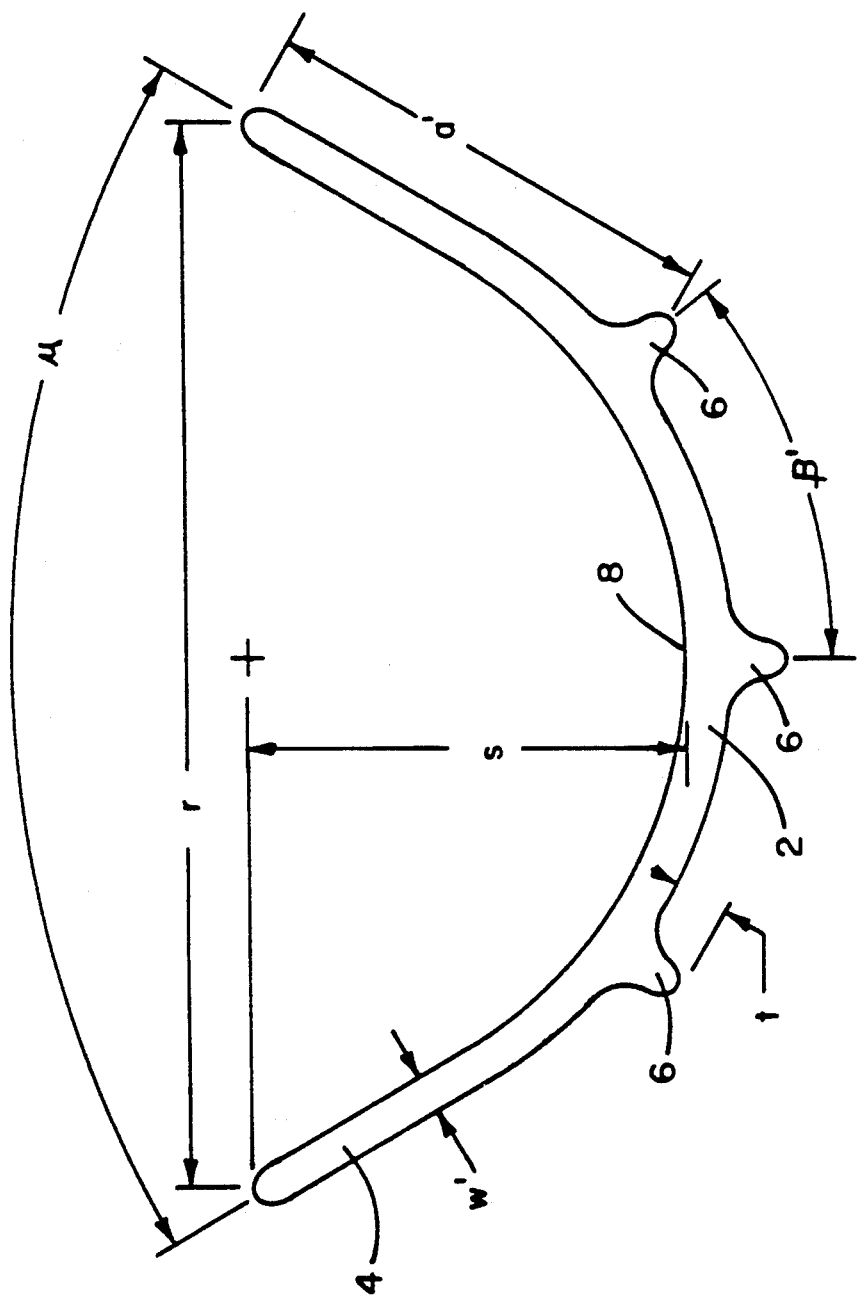
FIG. 1 is a schematic representation of a "U" shaped filament cross-section with stabilizing legs.

In reference to FIG. 1 of the drawings, the "U" shaped filament cross-section with stabilizing legs is made up of a curved section 2 containing stabilizing legs 6 and a straight section 4. The width of the filament cross-section is about 3 to about 15 microns and is noted by the letter w'. The angle between the stabilizing legs 6, $\beta'$, is about 10° to about 60°. There is an acute angle formed by intersection of the extension of the straight portions 4 of the filament. Such angle $\mu$ is 0° to about 70°. The length of the straight section 4 of the filament is about 50 to about 200 microns and is noted by the letter a'. The perpendicular distance from a line connecting the outer extremities of the straight sections 4 and the concave surface 8 of the filament, s, is 20 to 100 microns. The linear distance between the ends of the straight sections 4 of the filament, r, is 30 to 300 microns. The length of a stabilizing leg 6, t, is about 3 to about 15 microns. The stabilizing legs 6 may be different lengths as long as the length of each individual stabilizing leg is within the defined critical range. Preferably, for maintaining the curved section 2 of the filament, the stabilizing legs 6 are substantially equal in length. While the number of stabilizing legs 6, n, may be 3 to 6, only three stabilizing legs 6 are shown. In the case of 3 or 5 stabilizing legs, there is a stabilizing leg 6 on the vertical axis of symmetry and the other stabilizing legs 6 are substantially symmetrically spaced around the vertical axis of symmetry. In the case of 4 or 6 stabilizing legs, the stabilizing legs 6 are substantially symmetrically spaced around the vertical axis of symmetry. The stabilizing legs 6 serve to maintain the curved section 8 of the "U" shaped filament.

Figure 2:
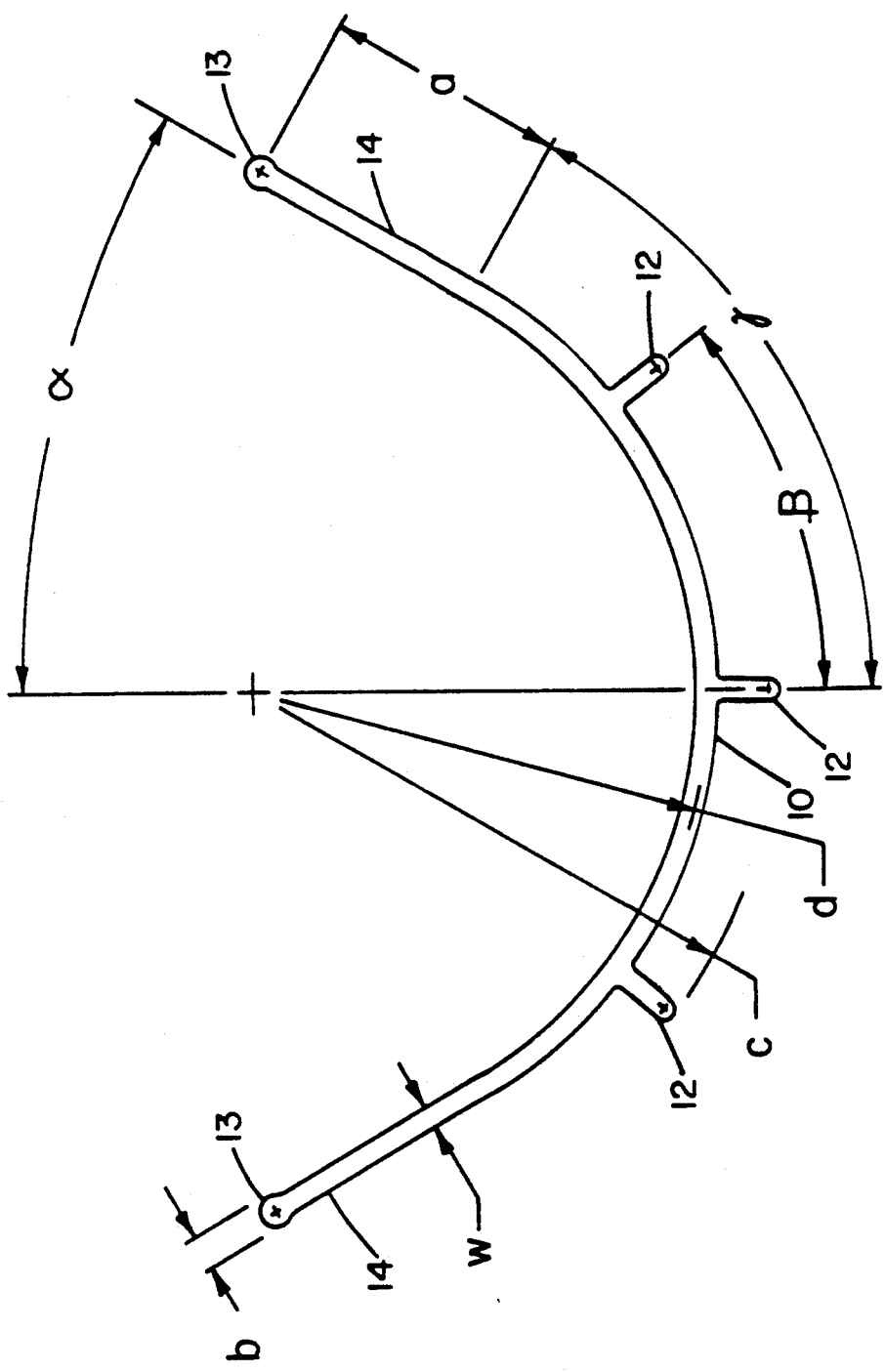
FIG. 2 is a schematic representation of a "U" shaped orifice of a spinneret with stabilizing legs useful for producing a spontaneously transportable filament.

In reference to FIG. 2 of the drawings, the "U" shaped orifice of a spinneret with stabilizing legs is made up of a curved section 10 containing stabilizing legs 12 and a straight section 14. The width of the orifice, w, is about 65 to about 120 microns. The angle between the vertical axis of symmetry and the straight section 14 of the orifice, $\alpha$, is 0° to about 60°. The angle between the stabilizing legs 12, $\beta$, is about 10° to about 60°. The angle $\gamma$ is about 10° to about 70° which is one-half the angle subtended by the curved section 10 of the orifice. The length of the straight section 14 of the orifice, a, is about 5 w to about 50 w. The diameter at the extremity of the orifice, b, which is in the shape of a circle 13, is about 1.1 w to about 2.5 w. The linear distance between the vertex on the vertical axis of symmetry and the extremity of a stabilizing leg 12, c, is about 15 w to about 55 w. The linear distance between the vertex on the vertical axis of symmetry and the center of the orifice in the curved section 10, d, is about 10 w to about 50 w. The length of a stabilizing leg 12, c−d, is about 3 w to about 10 w. The stabilizing legs 12 may be different lengths as long as the length of each individual stabilizing leg 12 is within the defined critical range. Preferably, for maintaining the curved section 10 of a filament extruded from such orifice, the stabilizing legs 12 are substantially equal in length. While the number of stabilizing legs 12, n, may be 3 to 6, only three stabilizing legs 12 are shown. In the case of 3 or 5 stabilizing legs, there is a stabilizing leg 12 on the vertical axis of symmetry and the other stabilizing legs 12 are substantially symmetrically spaced around the vertical axis of symmetry. In the case of 4 or 6 stabilizing legs, the stabilizing legs 12 are substantially symmetrically spaced around the vertical axis of symmetry.

Figure 3:
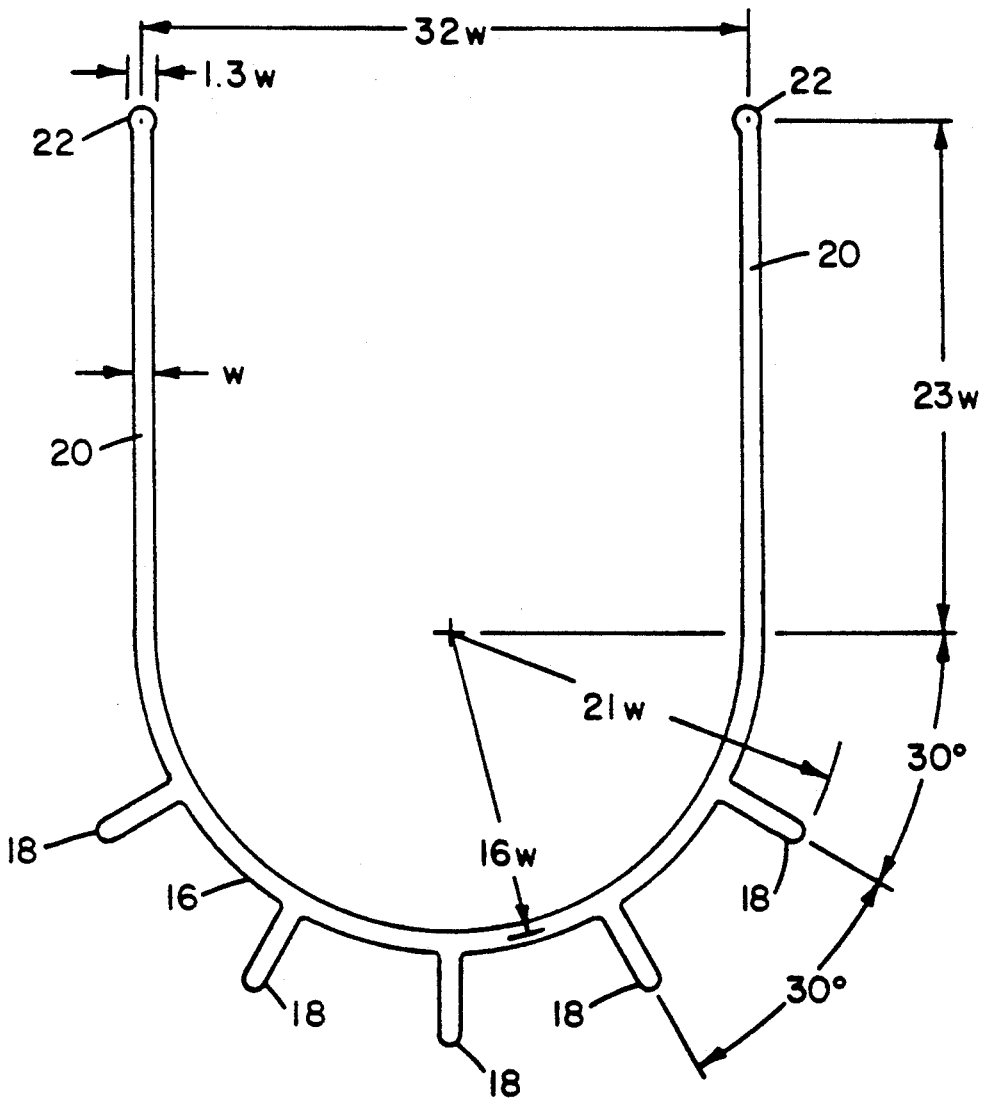
FIG. 3 is a schematic representation of a preferred "U" shaped orifice with stabilizing legs of a spinneret useful for producing a spontaneously transportable fiber.

In reference to FIG. 3 of the drawings, the "U" shaped orifice of a preferred spinneret with stabilizing legs is made up of a curved section 16 containing stabilizing legs 18 and a straight section 20. The width of the orifice, w, is about 84 microns. The angle between the vertical axis of symmetry and the straight section 20 of the orifice, $\alpha$, is 0°. The angle between the stabilizing legs 18, $\beta$, is about 30°. The angle $\gamma$ is about 60°, which is one half the angle subtended by the curved section 16 of the orifice. The length of the straight section 20 of the orifice, a, is about 23 w. The diameter at the extremity of the orifice, b, which is in the shape of a circle 22, is about 1.3 w. The linear distance between the ends of the straight sections 20 of the orifice is about 32 w. The linear distance between the vertex on the vertical axis of symmetry and the extremity of a stabilizing leg 18, c, is about 16 w. The linear distance between the vertex on the vertical axis of symmetry and the center of the orifice in the curved section 16, d, is about 21 w. The length of each stabilizing leg 18, is about 5 w. The number of stabilizing legs 18 is 5. A stabilizing leg 18 is located on the vertical axis of symmetry and the other stabilizing legs 18 are substantially symmetrically spaced around the vertical axis of symmetry.

Figure 4:
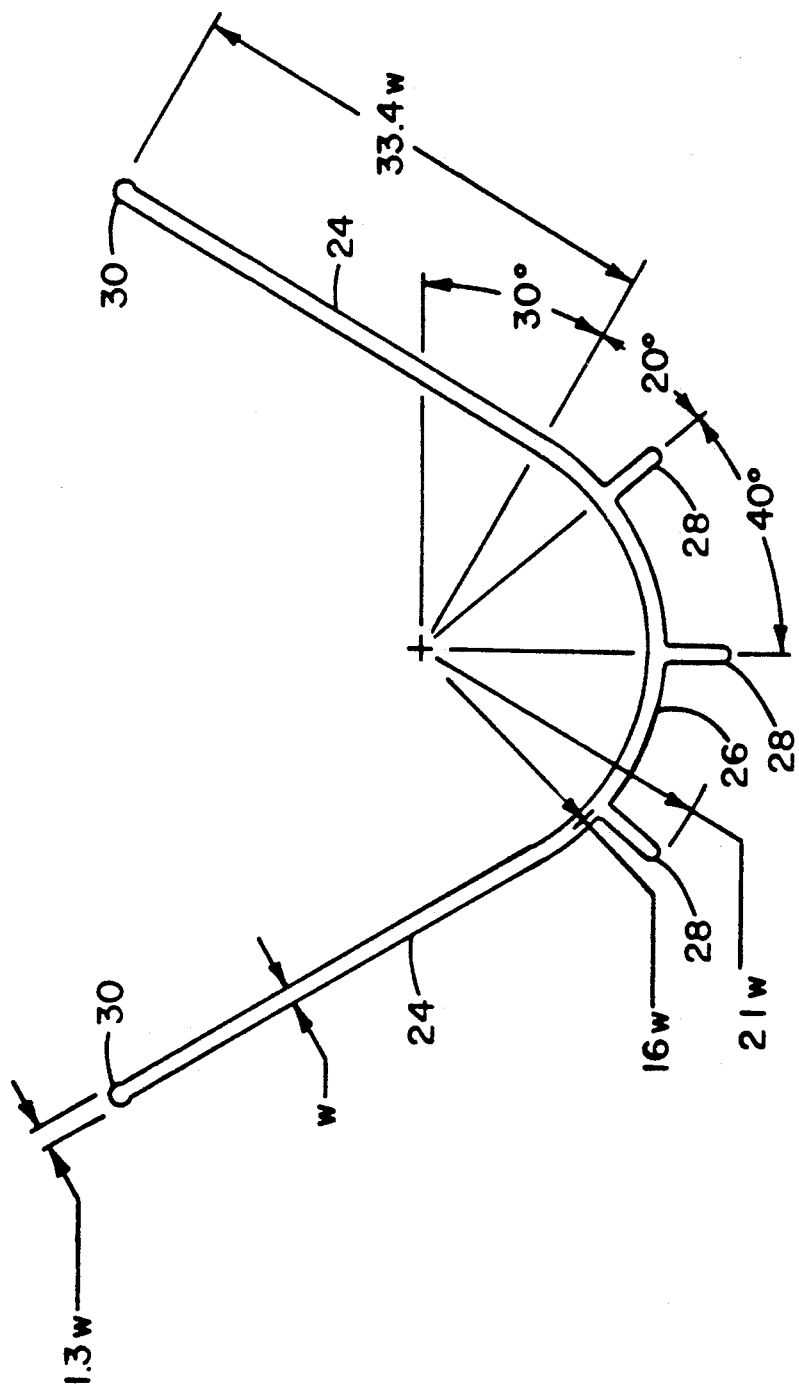
FIG. 4 is a schematic representation of a preferred "U" shaped orifice with stabilizing legs of a spinneret useful for producing a spontaneously transportable fiber.

In reference to FIG. 4 of the drawings, the "U" shaped orifice of a preferred spinneret with stabilizing legs is made up of a curved section 26 containing stabilizing legs 28 and a straight section 24. The width of the orifice, w, is about 84 microns. The angle between the vertical axis of symmetry and the straight section 24 of the orifice, $\alpha$, is about 30°. The angle between the stabilizing legs 28, $\beta$, is about 40°. The angle $\gamma$ is about 60°, which is one half the angle subtended by the curved section 26 of the orifice. The length of the straight section 24 of the orifice, a, is about 33.4 w. The diameter at the extremity of the orifice, b, which is in the shape of a circle 30, is about 1.3 w. The linear distance between the vertex on the vertical axis of symmetry and the extremity of a stabilizing leg 28, c, is about 16 w. The linear distance between the vertex on the vertical axis of symmetry and the center of the orifice in the curved section 26, d, is about 21 w. The length of each stabilizing leg 28, is about 5 w. The number of stabilizing legs 28 is 3. A stabilizing leg 28 is located on the vertical axis of symmetry and the other stabilizing legs 28 are substantially symmetrically spaced around the vertical axis of symmetry.

Figure 5:
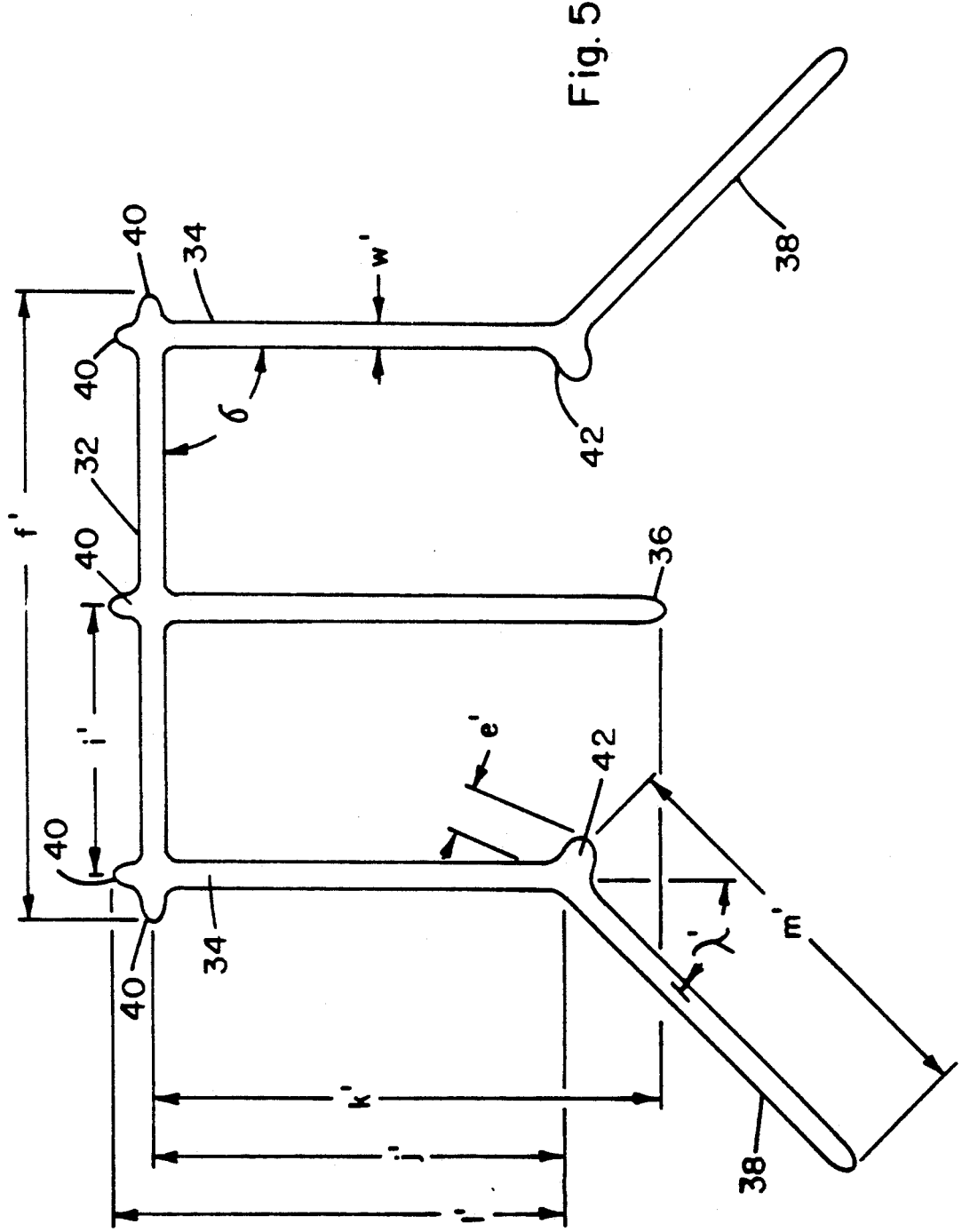
FIG. 5 is a schematic representation of a "E" shaped filament cross-section with stabilizing legs.

In reference to FIG. 5 of the drawings, the "E" shaped filament cross-section with stabilizing legs is made up of a backbone 32, two outer ribs 34, an inner rib 36, two rib extensions 38 and stabilizing legs 40 and 42. Stabilizing legs 40 are located on the backbone 32. Stabilizing legs 42 are located at the intersection of the outer rib 34 and rib extension 38. The stabilizing legs serve to maintain the straight sections of the "E" shaped filament. The width of the filament cross-section is about 3 to about 15 microns and is noted by the letter w'. The angle between a linear extension of an outer rib 34 and rib extension 38, $\gamma'$, is 0° to about 45°. The angle between the backbone 32 and an outer rib 34, $\sigma$, is about 90° to about 120°. The length of a stabilizing leg 40 and 42 as measured from a center point in the filament, e', is about 1 to about 15 microns. The stabilizing legs 40 and 42 may be different lengths as long as the length of each individual stabilizing leg is within the defined critical range. Preferably, for maintaining the "E" shape of the filament, the stabilizing legs 42 located at the intersection of the outer rib 34 and rib extension 38 are 1 to 3 microns while the remaining stabilizing legs 40 located on the backbone 32 are 3 to 8 microns. The length of the backbone 32 of the filament including stabilizing legs 40 located on each end, f', is about 30 to about 100 microns. The linear distance between the center of an outer rib 34 and the center of the middle rib 36, i', is about 8 to about 50 microns. The linear distance between the point where the outer rib 34 intersects the rib extension 38 and the center of the backbone 32, j', is about 15 to about 100 microns. The linear distance between the extremity of the middle rib 36 and the center of the backbone 32, k', is about 15 to about 150 microns. The linear distance between the point where the outer rib 34 intersects the rib extension 38 and the extremity of the stabilizing leg located on the backbone 40, l', is about 18 to about 115 microns. The linear distance between the extremity of rib extension 38 and the point where the outer rib intersects the rib extension 38, m', is 15 to 100 microns. While the number of stabilizing legs 40 and 42, n', may be 5 or 7, only 7 are shown. In the case where $\lambda'$ equals 0 than the number of stabilizing legs is 5 since the outer rib 34 and rib extension 38 form a straight line.

Figure 6:
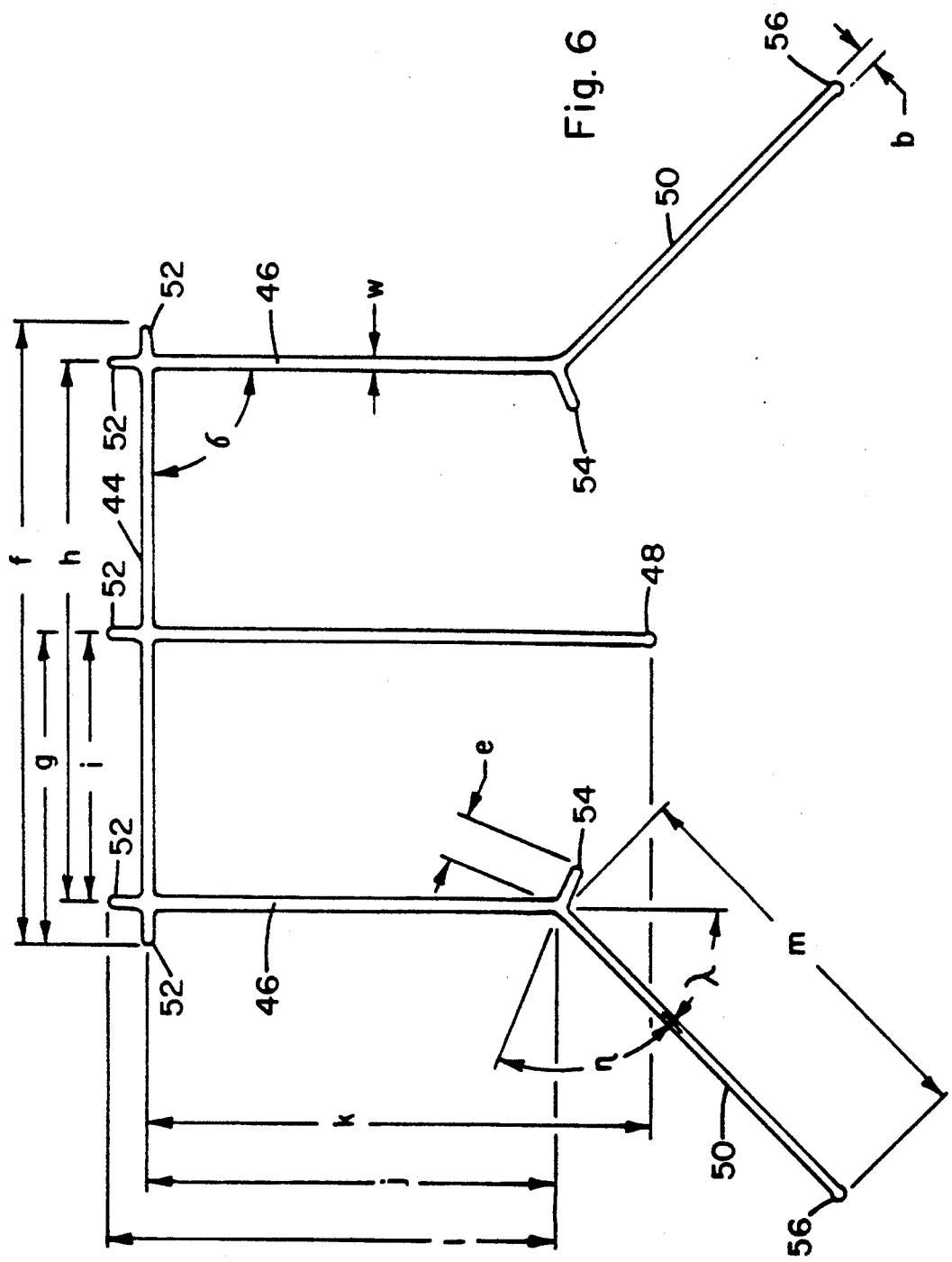
FIG. 6 is a schematic representation of an "E" shaped orifice of a spinneret with stabilizing legs useful for producing a spontaneously transportable fiber.

In reference to FIG. 6 of the drawings, the "E" shaped orifice of a spinneret with stabilizing legs is made up of a backbone 44, two outer ribs 46, an inner rib 48, two rib extensions 50 and stabilizing legs 52 and 54. The width of the orifice is about 65 to about 120 microns and is noted by the letter w. The angle between a linear extension of an outer rib 46 and rib extension 56, $\lambda$, is 0° to about 90°. The angle between the backbone 44 and an outer rib 46, $\alpha$, is about 90° to about 120°. The angle between the rib extension 50 and a linear extension of the stabilizing leg 54 located at the point where the outer rib 46 intersects the rib extension 50, η, is (180−λ)/2. The diameter at the extremity of the orifice which is in the shape of a circle 56, b, is about 1.1 w to about 2.5 w. The length of a stabilizing leg 52 and 54, e, is about 3 w to about 12 w. The stabilizing legs 52 and 54 may be different lengths as long as the length of each individual stabilizing leg is within the defined critical range. Preferably, for maintaining the "E" shape of a filament extruded through such orifice, the stabilizing legs 52 located at the intersection of the outer rib 46 and rib extension 50 are 3 w to 5 w while the remaining stabilizing legs 52 located on the backbone 44 are 5 w to 8 w. The length of the backbone 44 of the orifice including stabilizing legs 52 located on each end, f, is about 30 w to about 100 w. The linear distance between the center of the middle rib 48 and the outer extremity of the stabilizing leg 52 located on the backbone, g, is f/2. The linear distance between the center points of the two outer ribs 46, h, is f−2e. The linear distance between the center of an outer rib 46 and the center of the middle rib 48, i, is h/2. The linear distance between the point where the outer rib 46 intersects the rib extension 50 and the center of the backbone 44, j, is about 30 w to about 80 w. The linear distance between the extremity of the middle rib 48 and the center of the backbone 44, k, is (j−20)w to (j+50)w. The linear distance between the point where the outer rib 46 intersects the rib extension 50 and the extremity of the stabilizing leg 52 located on the backbone, l, is jw+ew. The linear distance between the extremity of rib extension 50 and the point where the outer rib 46 intersects the rib extension 50, m, is about 30 w to about 80 w. While the number of stabilizing legs 52 and 54, n', may be 5 or 7, only 7 are shown. In the where λ' equals 0 than the number of stabilizing legs is 5 since the outer rib 46 and rib extension 50 form a straight line.

Figure 7:
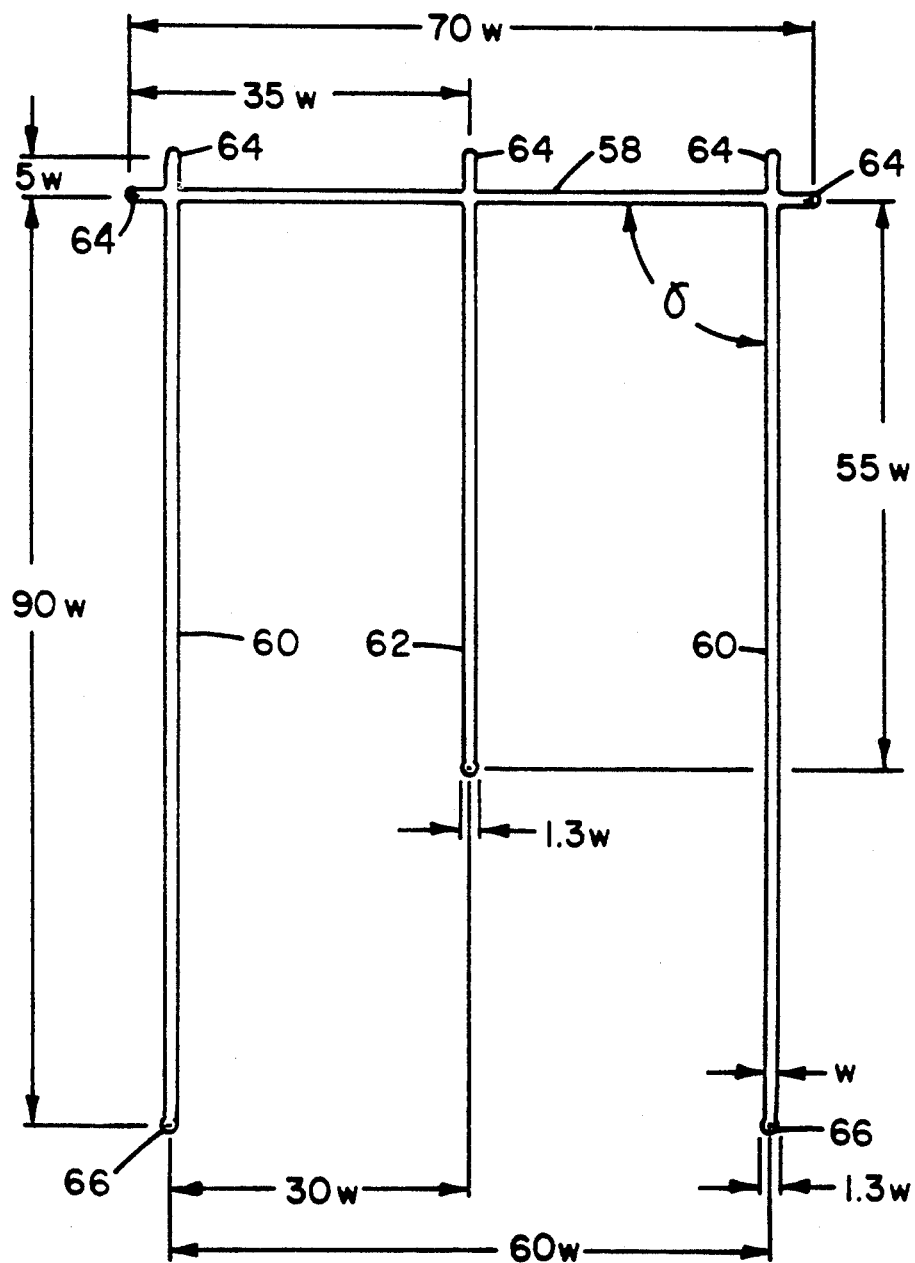
FIG. 7 is a schematic representation of a preferred "E" shaped orifice with stabilizing legs of a spinneret useful for producing a spontaneously transportable filament.

In reference to FIG. 7 of the drawings, the "E" shaped orifice of a preferred spinneret with stabilizing legs is made up of a backbone 58, two outer ribs 60, an inner rib 62 and stabilizing legs 64. The width of the orifice is about 84 microns and is noted by the letter w. The angle between the backbone 58 and an outer rib 60, σ, is about 90°. The diameter at the extremity of the orifice which is in the shape of a circle 66, b, is about 1.3 w. The length of a stabilizing leg 64, e, is about 5 w. The length of the backbone 58 of the filament including stabilizing legs 64 located on each end, f, is about 70 w. The linear distance between the center of the middle rib 62 and the outer extremity of the stabilizing leg 64 located on the backbone, g, is about 35 w. The linear distance between the center points of the two outer ribs 60, h, is about 60 w. The linear distance between the center of an outer rib 60 and the center of the middle rib 62, i, is about 30 w. The linear distance between the extremity of an outer rib 60 and the center of the backbone 58, about 90 w. The linear distance between the extremity of the middle rib 62 and the center of the backbone 58, k, is about 55 w. The number of stabilizing legs 64, n', is 5.

Copending commonly assigned U.S. patent application Ser. No. 07/736,267, filed Jul. 23, 1991 is hereby incorporated by reference for what it teaches about filaments capable of spontaneously transporting fluids including the use of the following equation to describe such filaments $$(1 - X\cos\theta_a) < 0,$$

In the above equation, $\theta_a$ is the advancing contact angle of water measured on a flat film made from the same material as the filament and having the same surface treatment, if any. The letter X is a shape factor of the filament cross-section that satisfies the following equation $$X = \frac{P_w}{4r + (\pi - 2)D}$$

In the above equation, $P_w$ is the wetted perimeter of the filament. The letter r is the radius of the circumscribed circle circumscribing the filament cross-section. The letter D is the minor axis dimension across the filament cross-section.

The term "spontaneously transportable" and derivative terms thereof refer to the behavior of a fluid in general and in particular a drop of fluid, typically water, when it is brought into contact with a single filament such that the drop spreads along the filament. Such behavior is contrasted with the normal behavior of the drop which forms a static ellipsoidal shape with a unique contact angle at the intersection of the liquid and the solid filament. The key factor is the movement of the location of the air, liquid, solid interface with time. If the interface moves just after contact of the liquid with the filament, then the filament is spontaneously transportable; if the interface is stationary, the filament is not spontaneously transportable. The spontaneously transportable phenomenon is visible to the naked eye for filaments having a denier per filament (dpf) of greater than 20. The filaments of the present invention preferably have a dpf of about 3 to about 1,000, more preferably 10 to 70.

Three important variables fundamental to liquid transport behavior are (a) surface tension of the liquid, (b) wettability or the contact angle of the liquid with the solid, and (c) geometry of the solid surface. The surface tension of the liquid refers to the attractive force exerted by the liquid molecules at the surface/air interface.

The second property of fundamental importance to the phenomena of liquid transport is the wettability or the contact angle between the liquid surface (gas liquid interface) and the solid surface (gas solid interface). Typically, a drop of liquid placed on a solid surface makes a contact angle with the solid surface. If the contact angle is less than 90°, then the solid is considered to be wet by the liquid. However, if the contact angle is greater than 90°, the solid is not wet by the liquid. Thus, it is desired to have a minimum contact angle for enhanced wetting which must be less than 90°. The contact angle also depends on surface inhomogeneities such as roughness, contamination, chemical/physical treatment of the solid surface, and surface free energy of the solid. The lower the surface energy of the solid, the more difficult it is to wet the solid by liquids having high surface tension. It is possible, however, to modify the surface energy of filament surfaces by appropriate lubricants/finishes to enhance liquid transport.

The third property of fundamental importance to the phenomena of liquid transport is the geometry of the solid surface. Although it is known that slots enhance fluid transport in general, the present inventors have discovered that particular "U" and "E" shaped orifices on filaments allow for more effective transport for a given vertical distance and linear distance of aqueous fluids in single filaments than filaments having other shapes. The present inventors have unexpectedly determined that stabilizing legs allow such "U" and "E" shaped filaments to maintain their shapes after being extruded through a spinneret.

In addition to being capable of transporting water, the filaments of the present invention are capable of spontaneously transporting other aqueous fluids and alcoholic fluids. Aqueous fluids are fluids containing at least 50 weight percent water and preferably at least 75 weight percent water. Most preferably, the aqueous fluids of the invention contain at least 90 weight percent water. Aqueous fluids include body fluids, such as blood, urine and perspiration, aqueous inks, and the like.

Alcoholic fluids are fluids containing at least 50 and preferably 70 weight percent of an alcoholic compound of the formula R—OH wherein R is an aliphatic or aromatic group containing up to 12 carbon atoms. Preferably R is an alkyl group of 1 to 6 carbon atoms. Examples of suitable alcoholic fluids include methanol, ethanol, n propanol and isopropanol.

The filaments of the present invention can be in the form of crimped or uncrimped tows or staple filaments containing a plurality of filaments. Helically crimping the filaments of the present invention involves the following steps: extruding a conventional PET filament forming polymer; passing the polymer through spinneret hole shapes; orienting said spinneret hole shapes to the cross flow quench air so that quenching occurs perpendicular to the major axis of the filament; controlling the quench air; applying a hydrophilic lubricant; taking up the filaments at conventional speeds; drafting the filaments using conventional drafting such as single steam stage in steam or two stage in water and steam; adding an additional amount of a hydrophilic lubricant; and relaxing the drawn filaments in a heated chamber to develop the helical crimp.

The full development of the helical crimp in the filaments of the present invention is realized by relaxing the filaments in heat. The temperature of the heating step must be greater than the glass transition temperature of the filaments. The helical crimp is formed due to differences in the orientation of the filament across the diameter of the cross-section. This difference in orientation is built into the filament by following the steps listed in the process previously described. The greater the difference in orientation, the more likely that the filament will form a helical crimp. Preferably the number of crimps/inch in the filament is greater than 2 and the crimp amplitude is less than 2 mm.

The orifices used to make the "U" and "E" shaped filament cross-sections with stabilizing legs disclosed herein, may be used to extrude therethrough any polymer capable of being spun into filaments. Illustrative of polymers which may be utilized in this invention are poly(ethylene terephthalate), poly(1,4-cyclohexylenedimethylene terephthalate), poly(butylene terephthalate), polypropylene, nylon, HYDROFIL nylon, and derivatives of cellulose such as organic esters of cellulose, for example diacetate and triacetate. The preferred polymer for use in the invention is poly(ethylene terephthalate) having an inherent viscosity of about 0.6 or higher.

Certain filaments require a hydrophilic lubricant to be applied to the surface thereof to obtain the spontaneous transportability property. Hydrophilic lubricants provide good wetting of filament surfaces and yield high adhesion tension at the surface of the filament. The hydrophilic lubricant should bind tightly to the filament surface and at the same time present high hydrophilicity to water. For example, it has been determined that when poly(ethylene terephthalate) is used as the polymer than a hydrophilic lubricant is necessary to obtain spontaneously transportable filaments. In contrast, however, filaments prepared using HYDROFIL nylon spontaneously transport aqueous fluids without a hydrophilic lubricant. Examples of preferred hydrophilic lubricants are:

(1) Lubricant which contains 49% polyethylene glycol (PEG) 600 monolaurate, polyoxyethylene (13.64) monolaurate, 49% polyethylene glycol (PEG) 400 monolaurate, polyoxyethylene (9.09) monolaurate, and 2% 4-cetyl-4-ethylmorpholinium ethosulfate (antistat);

(2) Hypermer A109 available from ICI Americas, Inc., which is a modified polyester surfactant;

(3) Milease T available from ICI Americas, Inc. which is a soil release agent comprising polyester, water, and other ingredients;

(4) Brij 35 available from ICI Americas, Inc. which is a polyoxyethylene (23) lauryl ether;

(5) Brij 99 available from ICI Americas, Inc. which is a polyoxyethylene (20) oleyl ether;

(6) G-1300 available from ICI Americas, Inc. which is a polyoxyethylene glyceride ester, a nonionic surfactant;

(7) G-1350 available from ICI Americas, Inc., a polyoxylene polyoxypropylene sorbitan linoleic phthalic ester; and (8) RACALUB PC available from ICI Americas, Inc. which is a soil release agent containing polyester, water, and other ingredients.

Such hydrophilic lubricants are uniformly applied at a level of at least 0.05 weight percent, with 0.1 to 2 weight percent being preferred.

The filaments of the present invention may be incorporated into an absorbent article in which it is desired to move or transport fluids. Such absorbent articles include, but are not limited to, diapers, incontinence pads, feminine hygiene napkins, catamenials, tampons, wipes, sweat absorbing headbands or wristbands, surgical sponges, wound dressings, sweat absorbing insoles for footwear, general purpose wiping articles, fabric softener strips for use in clothes dryers, wound drains, surgical drains, towels, geotextiles, athletic clothing such as athletic socks and jogging suits, cosmetic applicators, furniture polish applicators, pap smear samplers, throat culture samplers, blood analyzer test elements, household and industrial deodorizers, humidifier fabrics, moist filter media, orthopaedic cast liners, and the like.

An absorbent article of the present invention contains two or more filaments. At least part of the filaments are located near the center of the absorbent article and at least part of the same filaments are located away from the center of the absorbent article. The term "near the center" of the absorbent article means the geometric center and the area consisting of 50 area percent of the total article immediately surrounding the geometric center. The term "away from the center" of the absorbent article means the remaining area that is not near the center of the article. The filaments are capable of being in contact with an aqueous or alcoholic fluid for at least 10 seconds.

One or more sinks are present near the end of a filament which consists of the end 10% of the length of the filament, which are in contact with the filaments. The term "sink" refers to a structure which has a greater affinity for the aqueous or alcoholic fluid than the filament. The filament acts as a conduit to the sink until such time as the source dries up. It is clear that the locations of the sinks need to be removed from the location of the source if significant movement of fluid is desired (e.g., outer area of the diaper). Preferred sinks are fluff pulp, chemically modified fluff pulp, superabsorbant material, and combinations thereof.

The filaments of this invention may be prepared by techniques known in the art. A preferred process involves heating a polymer capable of forming a filament at or above its melting point followed by extruding said polymer through at least one spinneret having at least one orifice with dimensions as described herein. The filament may be drafted and/or thermally stabilized. The filament thus formed may then optionally be treated with a hydrophilic lubricant.

The materials and testing procedures used for the results shown herein are as follows:

Inherent viscosity (I.V.) was measured at 23° C. using 0.50 grams of polymer per 100 mL of a solvent consisting of 60% by weight phenol and 40% by weight tetrachloroethane.

Spontaneous surface transportation of an aqueous solution on filaments was tested using Syltint Poly Red ®, obtained from Milliken Chemicals, which is 80 weight percent water and 20 weight percent red colorant.

The invention will be further illustrated by a consideration of the following examples, which are intended to be exemplary of the invention. All parts and percentages in the examples are on a weight basis unless otherwise stated.

EXAMPLE 1

This example involves the use of a spinneret having "U" shaped orifices with stabilizing legs.

Poly(ethylene terephthalate) polymer having an inherent viscosity of 0.80 was dried to a moisture level of ≦0.003 weight percent in a Paterson Conaform dryer at 120° C. for eight hours. The polymer was extruded at 286° C. with a take up speed of 1,000 m/min through an Egan extruder, 1.5 inch diameter, with a length to diameter ratio of 28:1. A typical denier/filament was 40. The polymer throughput was about 7 pounds/hour. The air quench system has a cross flow configuration. The quench air velocity at the top of the screen was an average of 294 ft/minute. At a distance of about 7 inches from the top of the screen the average velocity of the quench air was about 285 ft/minute, and at a distance of about 14 inches from the top of the screen the average quench air velocity was about 279 ft/minute. At about 21 inches from the top of the air screen the average air velocity was about 340 ft/minute. The rest of the screen was blocked. RACALUB PC, a hydrophilic lubricant, in the form of an emulsion was applied at a level of 0.6% by means of two ceramic kiss rolls. Filaments of 20 dpf (denier per filament) were wound at 1,000 meters per minute (MPM) on a Barmag SW4SL winder.

Figure 11:
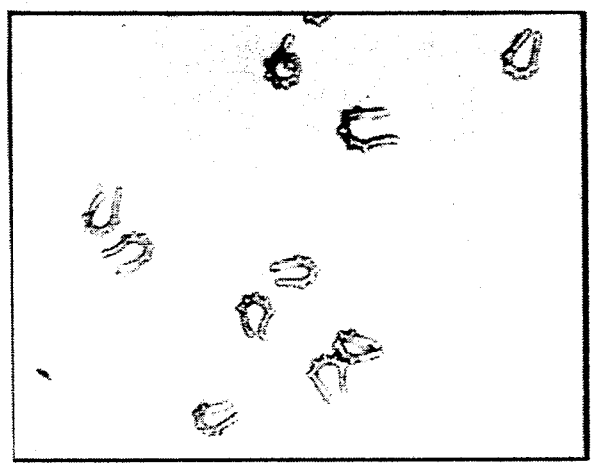
FIG. 11 is a photograph of a polyethylene terephthalate filament cross-section made using a spinneret having a "U" shaped orifice as illustrated in FIG. 3.

The poly(ethylene terephthalate) was extruded through an eight orifice spinneret wherein each orifice had dimensions as described in FIG. 3. The "X" value for the cross-sections was determined to be 1.47. Thus, 1−1.47 cos 20° equals −0.38. The filament, therefore, was spontaneously wettable which was confirmed by visual observation from the placement of dyed water on the surface thereof. A photograph of a cross-section of this filament is shown at 150× magnification in FIG. 11. FIG. 11 clearly shows that such filament cross-sections maintained their shape.

EXAMPLE 2

This example involves the use of a spinneret having "U" shaped orifices with stabilizing legs.

Figure 10:
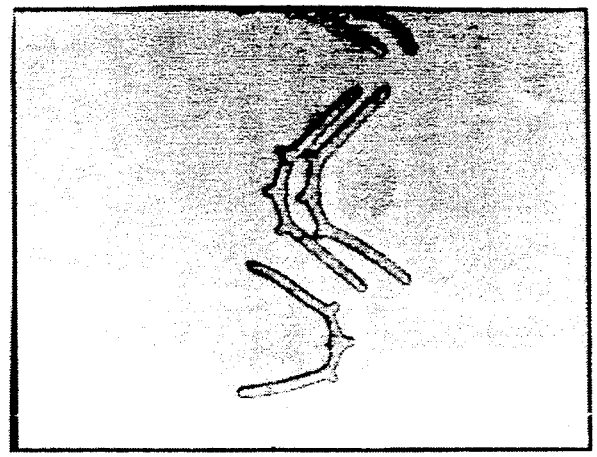
FIG. 10 is a photograph of a polyethylene terephthalate filament cross-section made using a spinneret having a "U" shaped orifice as illustrated in FIG. 4.

The poly(ethylene terephthalate) prepared in Example 1 was extruded through an eight orifice spinneret wherein each orifice had dimensions as described in FIG. 4. The "X" value for the cross-sections was determined to be 1.23. Thus, 1−1.23 cos 20° equals −0.16. The filament, therefore, was spontaneously wettable which was confirmed by visual observation from the placement of dyed water on the surface thereof. A photograph of a cross-section of this filament is shown at 150× magnification in FIG. 10. FIG. 10 clearly shows that such filament cross-sections maintained their shape.

EXAMPLE 3

This example involves the use of a spinneret having "U" shaped orifices with stabilizing legs.

The poly(ethylene terephthalate) prepared in spinneret wherein each orifice had the following dimensions: w, the width of the orifice, was 84 microns; $\alpha$, the angle between the vertical axis of symmetry and the straight section of the orifice, was 30°; $\beta$, the angle between the stabilizing legs, was 24°; $\gamma$, one half the angle subtended by the curved section of the orifice, was 60°; a, the length of the straight section of the orifice was 33.4 w; b, the diameter at the extremity of the orifice which is in the shape of a circle, was 1.3 w; c, the linear distance between the vertex on the vertical axis of symmetry and the extremity of a stabilizing leg, was 21 w; d, the linear distance between the vertex on the vertical axis of symmetry and the center of the orifice in the curved section, was 16 w; c d, the length of the stabilizing legs, was 5 w; and n, the number of stabilizing legs, was 5. A stabilizing leg was located on the vertical axis of symmetry and the other stabilizing legs were symmetrically spaced around the vertical axis of symmetry.

Figure 12:
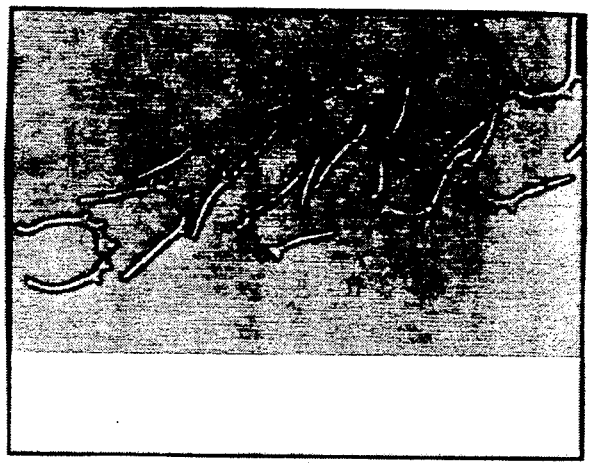
FIG. 12 is a photograph of a polyethylene terephthalate filament cross-section made using a "U" shaped spinneret orifice with stabilizing legs of the present invention.

The "X" value for the cross-sections was determined to be 1.59. Thus, 1−1.59 cos 20° equals −0.49. The filament, therefore, was spontaneously wettable which was confirmed by visual observation from the placement of dyed water on the surface thereof. A photograph of a cross-section of this filament is shown at 150× magnification in FIG. 12. FIG. 12 clearly shows that such filament cross-sections maintained their shape.

EXAMPLE 4

This example involves the use of a spinneret having "U" shaped orifices with stabilizing legs.

The poly(ethylene terephthalate) prepared in Example 1 was extruded through an eight orifice spinneret wherein each orifice had the following dimensions: w, the width of the orifice was 84 microns; $\alpha$, the angle between the vertical axis of symmetry and the straight section of the orifice, was 30°; $\beta$, the angle between the stabilizing legs, was 24°; $\gamma$, one half the angle subtended by the curved section of the of the orifice was 17.8 w; b, the diameter at the extremity of the orifice which is in the shape of a circle, was 1.3 w; c, the linear distance between the vertex on the vertical axis of symmetry and the extremity of a stabilizing leg, was 35.8 w; d, the linear distance between the vertex on the vertical axis of symmetry and the center of the orifice in the curved section, was 30.8 w; c−d, the length of the stabilizing legs, was 5 w; and n, the number of stabilizing legs, was 5. A stabilizing leg was located on the vertical axis of symmetry and the other stabilizing legs were symmetrically spaced around the vertical axis of symmetry.

Figure 13:
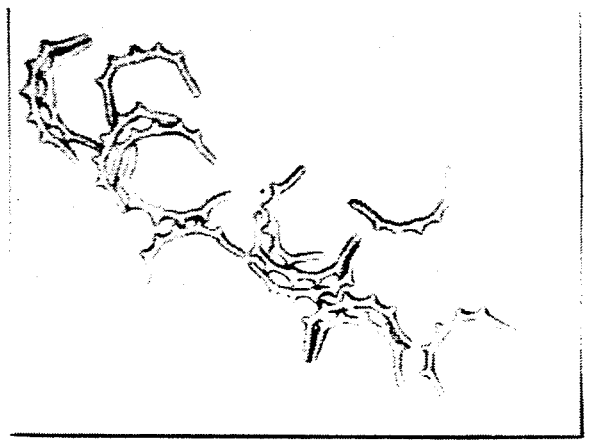
FIG. 13 is a photograph of a polyethylene terephthalate filament cross-section made using a "U" shaped spinneret orifice with stabilizing legs of the present invention.

The "X" value for the cross-sections was determined to be 1.14. Thus, 1−1.14 cos 20° equals −0.07. The filament, therefore, was spontaneously wettable which was confirmed by visual observation from the placement of dyed water on the surface thereof. A photograph of a cross-section of this filament is shown at 150× magnification in FIG. 13. FIG. 13 clearly shows that such filament cross-sections maintained their shape.

EXAMPLE 5

This example involves the use of a spinneret having "U" shaped orifices with stabilizing legs.

The poly(ethylene terephthalate) prepared in Example 1 was extruded through an eight orifice spinneret wherein each orifice had the following dimensions: w, the width of the orifice was 84 microns; α, the angle between the vertical axis of symmetry and the straight section of the orifice, was 30°; β, the angle between the stabilizing legs, was 40°; γ, one half the angle subtended by the curved section of the orifice, was 60°; a, the length of the straight section of the orifice was 17.8 w; b, the diameter at the extremity of the orifice which is in the shape of a circle, was 1.3 w; c, the linear distance between the vertex on the vertical axis of symmetry and the extremity of a stabilizing leg, was 35.8 w; d, the linear distance between the vertex on the vertical axis of symmetry and the center of the orifice in the curved section, was 30.8 w; c−d, the length of a stabilizing leg, was 5 w; and n, the number of the stabilizing legs, was 3. A stabilizing leg was located on the vertical axis of symmetry and the other stabilizing legs were symmetrically spaced around the vertical axis of symmetry.

Figure 9:
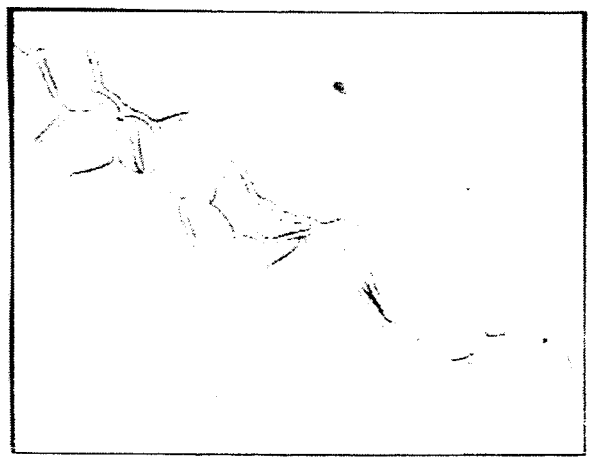
FIG. 9 is a photograph of a polyethylene terephthalate filament cross-section made using a "U" shaped spinneret orifice with stabilizing legs of the present invention.

The "X" value for the cross-sections was determined to be 1.03. Thus, 1−1.03 cos 20° equals 0.03. Because of variations in these filament shapes, some of the filaments exhibited spontaneous wettability and some did not. Collectively such filaments were a poor example of spontaneous wettability. A photograph of a cross-section of this filament is shown at 150× magnification in FIG. 9. FIG. 9 shows that such filament cross-sections maintained their shape.

EXAMPLE 6

This example is a comparison example using a spinneret having "U" shaped orifices without stabilizing legs.

The poly(ethylene terephthalate) prepared in Example 1 was extruded through an eight orifice spinneret wherein each orifice had the following dimensions: w, the width of the orifice, was 84 microns; α, the angle between the vertical axis of symmetry and the straight section of the orifice, was 20°; γ, one half the angle subtended by the curved section of the orifice, was 60°; a, the length of the straight section of the orifice was 25 w; b, the diameter at the extremity of the orifice which is in the shape of a circle, was 1.3 w; d, the linear distance between the vertex on the vertical axis of symmetry and the center of the orifice in the curved section, was 16 w.

Figure 14:
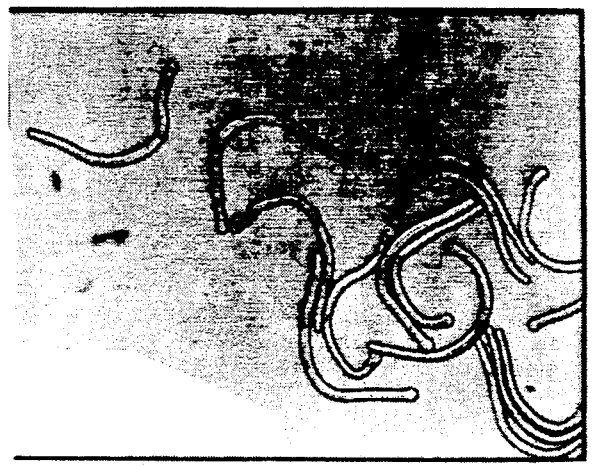
FIG. 14 is a photograph of a polyethylene terephthalate filament cross-section made using a spinneret having an "U" shaped orifice without stabilizing legs.

The "X" value for the cross-sections was determined to be 1.13. Thus, 1−1.13 cos 20° equals −0.06. The filament, therefore, was spontaneously Wettable Which was confirmed by visual observation from the placement of dyed water on the surface thereof. A photograph of a cross-section of this filament is shown at 150× magnification in FIG. 14. FIG. 14 shows that such filament cross-sections do not maintain their shape as uniformly as the sections with stabilizing legs.

EXAMPLE 7

This example involves the use of a spinneret having "E" shaped orifices with stabilizing legs.

Figure 15:
FIG. 15 is a photograph of a polyethylene terephthalate filament cross-section made using a spinneret having an "E" shaped orifice as illustrated in FIG. 7.

The poly(ethylene terephthalate) prepared in Example 1 was extruded through an eight orifice spinneret wherein each orifice had dimensions as described in FIG. 7. The "X" value for the cross-sections was determined to be 1.56. Thus, 1−1.56 cos 20° equals −0.47. The filament, therefore, was spontaneously wettable which was confirmed by visual observation from the placement of dyed water on the surface thereof. A photograph of a cross-section of this filament is shown at 150× magnification in FIG. 15. FIG. 15 clearly shows that such filament cross-sections maintained their shape.

EXAMPLE 8

This example is a comparison example using a spinneret having "E" shaped spinneret orifices with stabilizing legs. The dimensions of the orifices, however, fall outside the critical dimensions set forth in FIG. 6 for "E" shaped spinnerets with stabilizing legs. Specifically, the length of the stabilizing legs located on the backbone are not long enough to support the two outer ribs.

Figure 8:
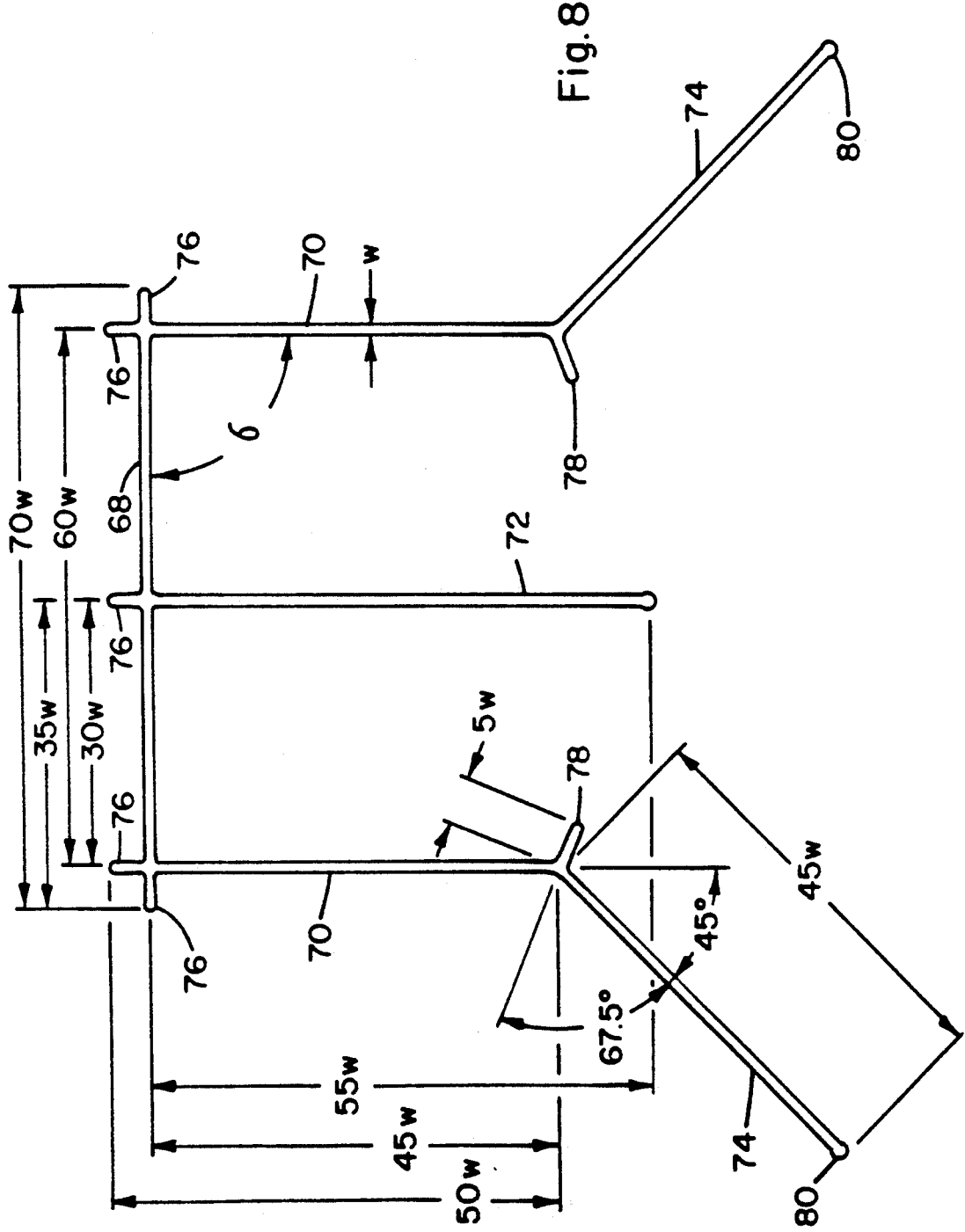
FIG. 8 is a schematic representation of a preferred "E" shaped orifice with stabilizing legs of a spinneret useful for producing a spontaneously transportable filament.
Figure 16:
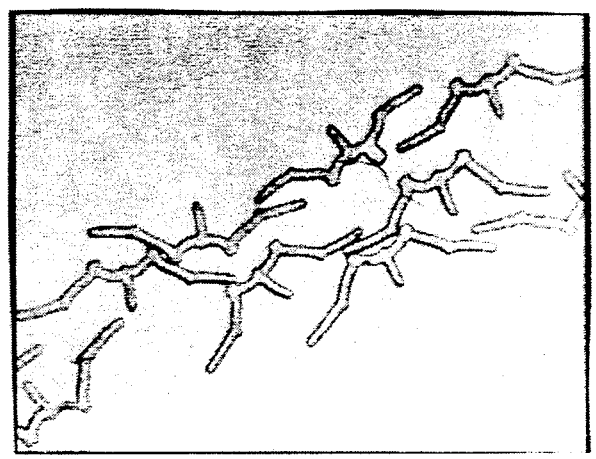
FIG. 16 is a photograph of a polyethylene terephthalate filament cross-section made using a spinneret having an "E" shaped orifice with dimensions that fall outside the dimensions set forth in FIG. 5.

The poly(ethylene terephthalate) prepared in Example 1 was extruded through an eight orifice spinneret wherein each orifice had dimensions as described in FIG. 8. The "X" value for the cross-sections was determined to be 1.50. Thus, 1−1.50 cos 20° equals −0.41. The filament, therefore, was spontaneously wettable which was confirmed by visual observation from the placement of dyed water on the surface thereof. A photograph of a cross-section of this filament is shown at 150× magnification in FIG. 16. FIG. 16 clearly shows that such filament cross-sections do not maintained their shape which means that the length of the stabilizing legs at the intersection of the outer rib and backbone needs to be increased in the spinneret orifice.

Many variations will suggest themselves to those skilled in this art in light of the above detailed description. All such obvious modifications are within the full intended scope of the appended claims.

What is claimed is:

1. A synthetic filament having a "U" or "E" shaped cross-section with stabilizing legs which is capable of spontaneously transporting water on the surface thereof wherein said filament satisfies the equation $$(1 - X \cos \theta_a) < 0,$$

wherein $\theta_a$ is the advancing contact angle of water measured on a flat film made from the same material as the filament and having the same surface treatment, if any, and X is a shape factor of the filament cross-section that satisfies the following equation $$X = \frac{P_w}{4r + (\pi - 2)D}$$

wherein $P_w$ is the wetted perimeter of the filament;

r is the radius of he circumscribed circle circumscribing the filament cross-section; and D is the minor axis dimension across the filament cross-section; provided said "U" shaped filament with stabilizing legs comprising a curved section containing stabilizing legs and two straight sections, wherein w', the width of the filament, is 3 to 15 microns; β', the angle between the stabilizing legs, is 10° to 60°; μ, the acute angle formed by intersection of extension of straight portions of the filament, is 0° to 70°; a', the length of the straight section of the filament is 50 to 200 microns; r, the linear distance between the ends of the straight sections of the filament, is 30 to 300 microns; s, the perpendicular distance from a line connecting the outer extremities of the straight sections and the concave surface of the filament, is 20 to 100 microns; t, the length of a stabilizing leg, is independently 3 to 15 microns; and n, the number of stabilizing legs, is 3 to 6; provided that when n is equal to 3 or 5, there is a stabilizing leg on the vertical axis of symmetry and the other stabilizing legs are substantially symmetrically spaced around the vertical axis of symmetry; and when n is equal to 4 or 6, the stabilizing legs are substantially symmetrically spaced around the vertical axis of symmetry; and said "E" shaped filament with stabilizing legs comprising a backbone, two outer ribs, an inner rib, two rib extensions and stabilizing legs, wherein w', the width of the filament, is 3 to 15 microns; λ', the angle between a linear extension of an outer rib and rib extension, is 0° to 45°; σ, the angle between the backbone and an outer rib, is 90° to 120°; e', the length of a stabilizing leg as measured from a center point in the filament, is independently 1 to 15 microns; f', the length of the backbone of the filament including stabilizing legs located on each end is 30 to 100 microns; i', the linear distance between the center of an outer rib and the center of the middle rib, is 8 to 50 microns; j', the linear distance between the point where the outer rib intersects the rib extension and the center of the backbone, is 15 to 100 microns; k', the linear distance between the extremity of the middle rib and the center of the backbone, is 15 to 150 microns; l', the linear distance between the point where the outer rib intersects the rib extension and the extremity of the stabilizing leg located on the backbone, is 18 to 115 microns; m', the linear distance between the extremity of rib extension and the point where the outer rib intersects the rib extension, is 15 to 100 microns; n', the number of stabilizing legs, is 4 or 6; provided that when λ' equals 0, n is 4.

2. The filament of claim 1 having a single filament denier of between 3 and 1,000.

3. The filament of claim 3 having a single filament denier of between 10 and 70.

4. The filament of claim 1 which is made of a material selected from the group consisting of polyester, polypropylene, polyethylene, cellulose ester, nylon and combinations thereof.

5. The filament according to claim 4 wherein the polyester comprises repeat units of ethylene terephthalate as the major component.

6. The filament of claim 1 having coated thereon a hydrophilic lubricant.

7. The filament of claim 6 wherein the hydrophilic lubricant is selected from the group consisting of
   (1) 49% polyethylene glycol 600 monolaurate, polyoxyethylene (13.64) monolaurate, 49% polyethylene glycol (PEG) 400 monolaurate, polyoxyethylene (9.09) monolaurate, and 2% 4-cetyl-4-ethylmorpholinium ethosulfate;
   (2) a modified polyester surfactant;
   (3) a soil release agent consisting of polyester, water and other ingredients;
   (4) polyoxyethylene lauryl ether;
   (5) polyoxyethylene oleyl ether;
   (6) polyoxyethylene glyceride ester, a nonionic surfactant;
   (7) a polyoxylene polyoxypropylene sorbitan linoleic phthalic ester; and
   (8) a soil release agent containing polyester, and water.

8. An absorbent article comprising two or more filaments of claim 1 wherein at least part of the filaments are located near the center of the absorbent article and at least part of the filaments are located away from the center of the absorbent article; and wherein the filaments are capable of being in contact with an aqueous fluid for at least 10 seconds near the center of the absorbent article.

9. An absorbent article comprising two or more filaments of claim 1 wherein at least part of the filaments are located near the center of the absorbent article and at least part of the filaments are located away from the center of the absorbent article; and wherein the filaments are capable of being in contact with an aqueous fluid for at least 10 seconds near the center of the absorbent article; and wherein away from the center of the absorbent article at least one sink is present that is in contact with at least one filament.

10. The absorbent article of claim 8 selected from the group consisting of diapers, incontinent briefs, feminine hygiene napkins, tampon, surgical sponges, wound dressings, and towels.

11. The absorbent article of claim 9 selected from the group consisting of diapers, incontinent briefs, feminine hygiene napkins, tampon, surgical sponges, wound dressings, and towels.

12. The absorbent article of claim 10 which is a diaper.

13. The absorbent article of claim 10 which is a incontinent brief.

14. The absorbent article of claim 10 which is a feminine hygiene napkin.

15. The absorbent article of claim 10 which is a tampon.

16. The absorbent article of claim 11 which is a diaper.

17. The absorbent article of claim 11 which is a incontinent brief.

18. The absorbent article of claim 11 which is a feminine hygiene napkin.

19. The absorbent article of claim 11 wherein the sink is selected from the group consisting of fluff pulp, chemically modified fluff pulp, superabsorbant material, and mixtures thereof.

20. A tow comprising a plurality of the filaments of claim 1.

21. The tow of claim 20 having a denier of about 2,000 to 400,000.

* * * * *